United States Patent [19]

Anderson

[11] Plant 4,317

[45] Oct. 17, 1978

[54] DWARF PEACH TREE (54-P-455)

[76] Inventor: Frederic W. Anderson, 826 W. 22nd St., Merced, Calif. 95340

[21] Appl. No.: 867,370

[22] Filed: Jan. 6, 1978

[51] Int. Cl.[2] ..... A01H 5/03
[52] U.S. Cl. ..... Plt./43
[58] Field of Search ..... Plt./43

*Primary Examiner*—Robert E. Bagwill
*Attorney, Agent, or Firm*—Roger B. Webster

[57] ABSTRACT

A genetically dwarf peach tree which is vigorous, spreading, and dense in growth with stocky, shaggy trunk and branches; foliated with large, acuminate, abruptly pointed leaves having a crenate, finely serrate margin, short petiole, and alternate, globose glands; and a regular and very productive bearer of large, uniform, symmetrical, globose, freestone fruit having yellow skin partially overspread with red, and yellow flesh which is firm, crisp, and meaty.

1 Drawing Figure

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of dwarf peach tree resulted from my endeavors in the conduct of such plant breeding program; such variety being embraced by Class 43, Plants, of the U.S. Patent Office Manual of Classification.

2. Prior Varieties

Among the existent varieties of peach trees which are known to me, I make particular reference to the Lovell (unpatented) mentioned hereinafter for the purpose of comparison.

ORIGIN OF THE VARIETY

The present variety of dwarf peach tree was originated by me in my experimental nursery and orchard, located as aforesaid, as a first generation cross between the Golden Glory dwarf peach (U.S. Plant Pat. No. 2,418) as the seed parent and the Bonanza dwarf peach (U.S. Plant Pat. No. 2,213) as the pollen parent.

ASEXUAL REPRODUCTION OF THE VARIETY

I asexually reproduced the variety by top-working on mature orchard trees in my said experimental orchard, and—in maturity—such reproductions ran true to the original tree in all respects.

SUMMARY OF THE VARIETY

The herein-claimed new and distinct variety of dwarf peach tree is vigorous, spreading, and dense in growth with stocky, shaggy trunk and branches; foliated with large, acuminate, abruptly pointed leaves having a crenate, finely serrate margin, short petiole, and alternate, globose glands; and a regular and very productive bearer of large, uniform, symmetrical, globose, freestone fruit having yellow skin partially overspread with red, and yellow flesh which is firm, crisp, and meaty.

The herein-claimed new and distinct variety of dwarf peach tree has the desirable characteristics—especially in the fruit—of the full size Lovell peach tree, yet—because of its low height—the tree of the present variety can be pruned, thinned, and the fruit harvested therefrom, more readily and much more economically.

BRIEF DESCRIPTION OF THE DRAWING

The drawing is an illustration, by photographic reproduction in color, of a twig with leaves, and separate fruit; one of the latter being halved with the stone remaining in one half.

DESCRIPTION OF THE VARIETY

The botanical details of this new and distinct variety of dwarf peach tree—with color definitions referenced to Maerz and Paul Dictionary of Color—are as follows:

Tree:
- *Class.*—Genetically dwarf.
- *Vigor.*—Vigorous.
- *Growth.*—Spreading.
- *Density.*—Dense.
- *Production.*—Very productive.
- *Bearing.*—Regular bearer.

Trunk:
- *Size.*—Stocky.
- *Texture.*—Shaggy.

Branches:
- *Size.*—Stocky.
- *Texture.*—Shaggy.

Leaves:
- *Size.*—Large. Average length — 7". Average width — 1⅝".
- *Form.*—Acuminate. Abruptly pointed.
- *Thickness.*—Medium.
- *Color.*—Top Side — Medium green (23-J-7). Under Side — Lighter green (22-L-7).
- *Margin.*—Crenate. Finely serrate.
- *Petiole.*—Short. Medium thickness.
- *Glands.*—Average number — 2 to 3. Usually on base of blade, sometimes on petiole. Alternate. Medium size. Globose.

Flower buds:
- *Size.*—Medium.
- *Length.*—Medium.

Flowers:
- *Blooming period.*—Feb. 22, 1977, - Mar. 7, 1977. Early, as compared with other varieties.
- *Size.*—Large.

Fruit:

*Maturity when described.*—Hard — Aug. 20, 1977.
*Date of first picking.*—Aug. 15, 1977.
*Date of last picking.*—Aug. 25, 1977.
*Size.*—Large. Uniform. Average diameter axially — $2\frac{3}{4}''$. Average transversely in suture plane — $2\frac{5}{8}''$.
*Form.*—Uniform. Symmetrical. Globose.
*Suture.*—Shallow. Extends from base to apex, with slight depression beyond pistil point.
*Ventral surface.*—Rounded strongly.
*Base.*—Rounded.
*Apex.*—Depressed.
*Pistil point.*—Wanting.

Skin:
*Thickness.*—Thick.
*Texture.*—Medium.
*Tendency to crack.*—None noted.
*Down.*—Moderate. Short.
*Color.*—Yellow (10-L-5) partially overspread with red (4-L-7).

Flesh:
*Juice.*—Moderate.
*Texture.*—Firm. Crisp. Meaty.
*Fibers.*—Few.
*Ripens.*—Evenly.
*Flavor.*—Subacid. Vinous.
*Aroma.*—Wanting.
*Eating quality.*—Good.
*Color.*—Yellow (10-L-4).

*Surface of pit cavity.*—Red (5-L-6) lightly streaked into flesh.

Stone:
*Type.*—Free.
*Size.*—Medium. Average length — $1\frac{1}{8}''$. Average length — $1''$. Average thickness — $\frac{5}{8}''$.
*Form.*—Oblong.
*Base.*—Straight.
*Apex.*—Rounded to acute.
*Sides.*—Equal.
*Ventral edge.*—Thin.
*Dorsal edge.*—Full, with broad groove throughout.
*Tendency to split.*—Slight.
*Color.*—Brown (8-L-7) with reddish shade.

Use: Market — local. Dessert. Culinary.
Keeping quality: Medium.
Resistance to insects and diseases: No unusual susceptibilities noted.
Shipping quality: Medium.

The dwarf peach tree and its fruit herein described may vary in slight detail due to climatic and soil conditions under which the variety may be grown; the present description being of the variety as grown in the Central Valley of Calif.

I claim:

1. A new and distinct variety of peach tree, substantially as illustrated and described, which, while having the desirable characteristics of the full-size Lovell, is—in comparison—genetically dwarf.

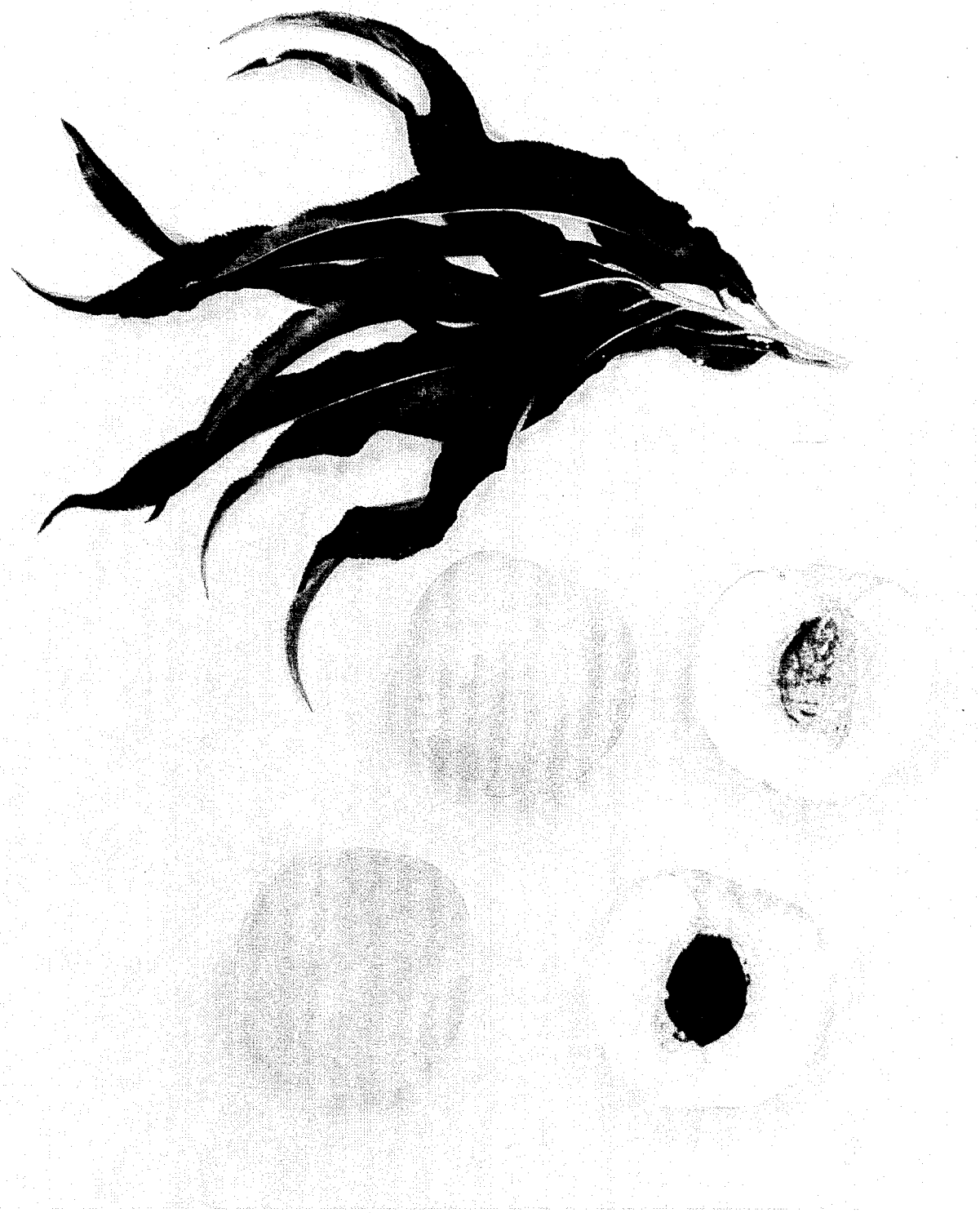

* * * * *